United States Patent [19]

Springer et al.

[11] Patent Number: 5,770,731

[45] Date of Patent: Jun. 23, 1998

[54] IMPROVEMENTS RELATING TO PRODRUGS

[75] Inventors: Caroline Joy Springer, Sutton; Richard Marais, London, both of United Kingdom

[73] Assignee: Cancer Research Campaign Technology Limited, London, United Kingdom

[21] Appl. No.: 586,637

[22] PCT Filed: Jul. 27, 1994

[86] PCT No.: PCT/GB94/01610

§ 371 Date: Apr. 19, 1996

§ 102(e) Date: Apr. 19, 1996

[87] PCT Pub. No.: WO95/03830

PCT Pub. Date: Feb. 9, 1995

[30] Foreign Application Priority Data

Jul. 27, 1993 [GB] United Kingdom ............... 9315494

[51] Int. Cl.$^6$ .................. C07D 243/24; C07D 261/06; C07D 207/40; C07D 313/04
[52] U.S. Cl. ................. 540/509; 548/547; 549/271; 549/293; 549/321; 558/248
[58] Field of Search ............................... 548/547

[56] References Cited

FOREIGN PATENT DOCUMENTS

| 535 730 | 4/1993 | European Pat. Off. . |
| 535 731 | 4/1993 | European Pat. Off. . |
| 547 669 | 6/1993 | European Pat. Off. . |
| 547 672 | 6/1993 | European Pat. Off. . |

OTHER PUBLICATIONS

Kohl et al. Science., vol. 260, No. 5116, pp. 1934–1937, Jun. 25, 1993.
Getz et al. J. Org. Chem. 1992, 57, 1702–1706.

*Primary Examiner*—Mark L. Berch
*Assistant Examiner*—Bruck Kifle
*Attorney, Agent, or Firm*—Spencer & Frank

[57] ABSTRACT

A prodrug of the general formula FTLi-(PRT)m, where m is an integer from 1 to 5; FTLi is a ras inhibitor such as a farnesyltransferase inhibitor compound, such as Ia, Ib, Ic; and PRT represents m protecting groups or a precursor thereof, such as compound XVI, which are capable of being cleaved from the ras inhibitor by the action of a enzyme.

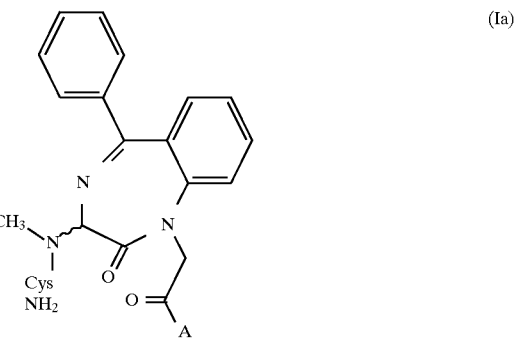

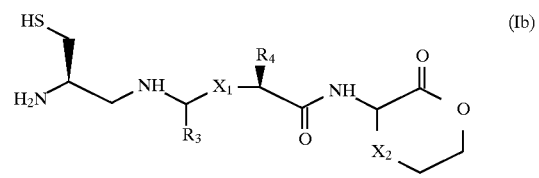

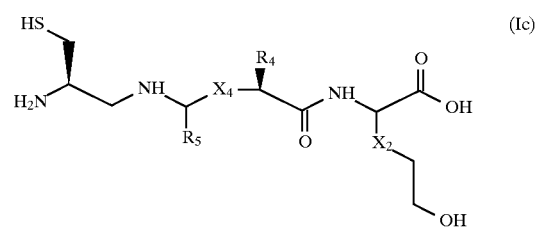

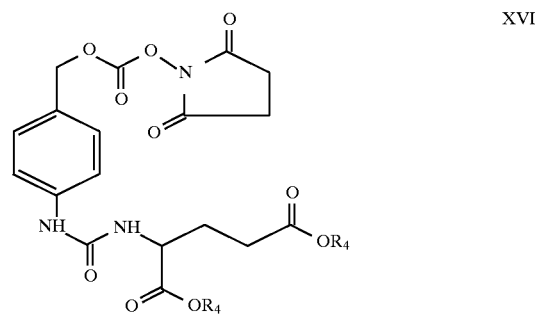

6 Claims, No Drawings

IMPROVEMENTS RELATING TO PRODRUGS

CROSS REFERENCE TO RELATED APPLICATIONS

This application is related to International Application No. PCT/GB94/01610 filed Jul. 27, 1994 and GB 9315494.6 filed Jul. 27, 1993, the priority date of which is claimed.

BACKGROUND OF THE INVENTION

1. Field of the Invention

The present invention relates to prodrugs and their use in the treatment of tumours.

2. Description of the Related Art

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

More recently, a similar approach ("VDEPT") has been proposed where in place of an antibody/enzyme conjugate, tumour cells are targeted with a viral vector carrying a gene encoding an enzyme capable of activating a prodrug. The gene may be transcriptionally regulated by tumour specific promoter or enhancer sequences. The viral vector enters tumour cells and expresses the enzyme, in order that a prodrug is converted to an active drug only in the vicinity of the tumour cells (Huber et al, Proc. Natl. Acac. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French Anderson, Annu. Rev. Biochem., 1993,62;191. The term "GDEPT" (gene-directed enzyme prodrug therapy) is used used to include both viral and non-viral delivery systems. The enzyme may be targeted to particular subcellular locations or expressed at the cell surface.

Although the GDEPT and ADEPT systems enhance the concentrations of anti-tumour agents which may be delivered to the site of a tumour, there is still a need to enhance the specificity of drug delivery. In both systems, active drug can be released into the environment of normal cells and cause damage. In the case of ADEPT, this can be caused by activation of prodrug by conjugates which have failed to localise at the tumour site. In GDEPT, transformation of normal tissue may lead to residual levels of expression of the enzyme away from the tumour or active drug may be released from tumour cells. Although ways to increase the specificity of the ADEPT system is disclosed in WO89/10140, there remains a continuing need to improve the level of ADEPT and GDEPT specificity.

Ras is often associated with transformation of cells. Oncogenic ras is over-expressed in a number of human tumours eg. over 50% of colon carcinoma and 90% of pancreatic carcinomas (Marsters et al, 1993, Science 260 1937–1942) also in lung tumours.

It has been shown that inhibition of oncogenic ras in cell culture leads to reversal of the transformed phenotype. Therefore the ability to develop specific inhibitors of ras may have great therapeutic application.

However, one potential pitfall with targeting ras, is the presence of normal non-mutated ras in all normal cells. In normal cells the role of ras is crucial. It is therefore essential to inhibit selectively only activated ras in transformed cells.

Recently, inhibitors of ras farnesyltransferase, which selectively inhibit farnesylation of oncogenic ras, have been described. (Kohl, Science, 260, 1934, 1993; James, ibid, 1937).

SUMMARY OF THE INVENTION

The present invention addresses such problems by the use of a novel class of prodrugs, which are prodrugs of ras inhibitors such as inhibitors of farnesyltransferase. This enzyme is essential for farnesylation of ras which is an absolute requirement for the transforming function of oncogenic ras (Gibbs, 1992, seminars in Cancer biol. 3, 383). The use of ras inhibitors such as farnesyltransferase inhibitors in ADEPT or GDEPT thus provides an increased level of specificity for the treatment of tumour cells. Prodrugs based upon farmesyltransferase inhbitors will be converted into farnesyltransferase inhibitors primarily at the site of a tumour, but at the same time release of farnesyltransferase inhibitors at other sites or from the tumour will not cause cytotoxicity comparable to the release of non-specific cytotoxic drugs.

DETAILED DESCRIPTION OF THE INVENTION

In one aspect, the present invention provides a prodrug of the general formula:

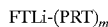

where FTLi is a ras inhibitor such as a farnesyltransferase inhibitor compound and PRT represents m protecting groups capable of being cleaved from the ras inhibitor by the action of an enzyme, where m is an integer from 1 to 5.

Suitable FTLi's include those described by James et al (ibid) and Kohl et al (ibid), and especially FTLi's of the general formula (Ia)

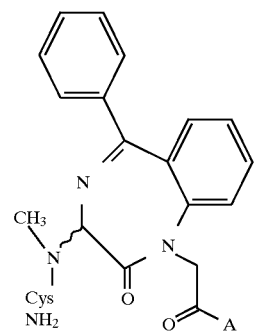

wherein Cys is cysteine; A is a group —NH.CH($R^1$).COO$R^2$ wherein $R^1$ is a naturally occurring amino acid side chain and $R^2$ is hydrogen, methyl or amino. Compounds of the formula Ia in which A is a leucine [—NH.CH($CH_2$CH($CH_3$)$_2$).COOH] group, a serine [—NH.CH($CH_2$OH).COOH] group, a methionine [—NH.CH($CH_2$$CH_2$SCH$_3$).COOH] group, or an amidated methionine [—NH.CH($CH_2$$CH_2$SCH$_3$).CONH$_2$] group are preferred. Compounds of formula Ia may be used as racemic mixtures or the isomers may be isolated.

Other suitable FLTi's include those of the formula (Ib) or (Ic):

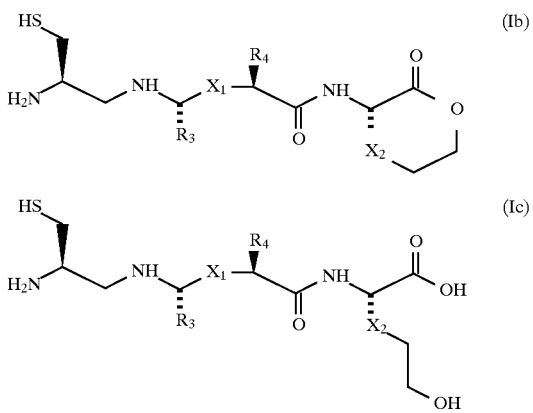

R$_3$ and R$_4$ are
  the side chains of naturally occurring amino acids (for example —CH$_3$, —CH(CH$_3$)$_2$, —CH$_2$CH(CH$_3$)$_2$, —CH(CH$_3$)CH$_2$CH$_3$, —CH$_2$OH, —CH$_2$CH$_2$SCH$_3$, —CH(OH)CH$_3$), including their oxidized forms (for example, methionine sulfoxide or methionine sulfone), or are substituted or unsubstituted aliphatic, aromatic or heteroaromatic groups, preferably cyclohexyl, phenyl, pyridyl, imidazolyl or saturated or unsaturated branched or straight chains of 2 to 8 carbon atoms optionally substituted with an aromatic or heteroaromatic ring;

X$_1$ is CH$_2$CH$_2$, trans CH═CH or CH$_2$NH; and

X$_2$ is (CH$_2$)$_n$ wherein n is 0, 1 or 2. Preferably R$_3$ and R$_4$ both represent CH(CH$_3$)CH$_2$CH$_3$.

Compounds of formula (Ib) or (Ic) wherein X$_1$ is —CH$_2$NH— can be obtained by the following general process. A compound of the formula (IX):

wherein Y$_1$ is a suitable protecting group, for example t-butoxycarbonyl, and wherein R$_3$ is defined as above, which may be prepared from the corresponding protected amino acid by formation of the Weinreb amide followed by reduction, preferably by LiAlH$_4$ in ether below −35° C., is reacted with the trifluroacetate salt of a compound of formula (X):

wherein R$_4$ is as defined above, in anhydrous DMF, followed by reduction, preferably with sodium triacetoxy borohydride to obtain a compound of formula (XI):

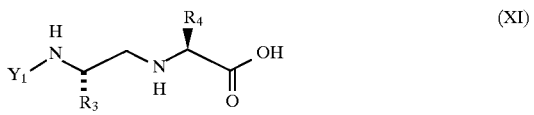

wherein Y$_1$, R$_3$ and R$_4$ are as defined above. The compound of formula (XI) is then reacted in the presence of triethylamine with a compound of formula (XII):

wherein X$_2$ is as defined above to obtain a compound of formula (XIII):

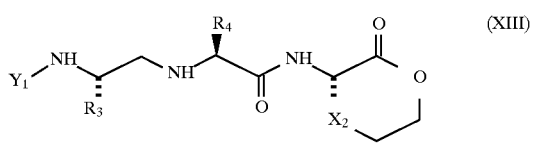

wherein Y$_1$, R$_3$, R$_4$, and X$_2$ are as defined above. This product is then deprotected, for example, by treatment with a solution of anhydrous hydrogen chloride in ethyl acetate at −25° C. and then reacted with a compound of formula (XIV):

wherein Y$_2$ and Y$_3$ are suitable protecting groups, for example, Y$_2$ is t-butoxycarbonyl and Y$_3$ is trityl, (compounds of formula (XIV) may be obtained from the corresponding protected cysteine by formation of the Weinreb amide followed by reduction, preferably by LiAlH$_4$ in ether at below −35° C.), to obtain after deprotection a compound of formula (Ib), which may then optionally be hydrolysed to obtain a compound of formula (Ic).

The above compounds of formula (Ib) or (Ic) wherein X is —CH$_2$NH— may also be obtained by reference to Kohl et al and James et al.

Compounds of formula (Ib) or (Ic) wherein X is CH$_2$CH$_2$ or trans CH═CH may be obtained by the process described in WO 94/09766.

FTLi's may be linked to any suitable protecting group which is removable by an enzyme. Examples of such groups include those found in WO88/07378 or in WO93/08288. For example, WO93/08288 describes "self immolative" prodrugs which can be activated by the action of a nitroreductase enzyme. These prodrugs are derivatives of p-nitrobenzyloxycarbonyl compounds.

The exact structure of the protecting group will depend upon the nature of the ADEPT or GDEPT system with which a ras inhibitor prodrug is to be used. It may be any suitable group which can be removed by an enzyme or modified by the enzyme in such a manner that the group is unstable and undergoes "self immolation" to provide the active ras inhibitor drug.

The number of protecting groups attached to each FTLi will depend in part upon the exact structure of the inhibitor compound. It will also depend upon the relative activity of the unprotected FTLi to the FTLi when different numbers of protecting groups are added, since if additional protecting groups will acheive a reduction in potency of the prodrug this will increase the ratio of activity of FTLi to FTLi-(PRT)$_m$.

Desirably, one or two protecting groups will be attached to each FTLi molecule to provide a compound of the invention, although more, e.g. 3, 4 or 5 groups may be added where the FTLi is of a structure which will allow this number to be linked.

Accordingly, prodrugs according to the invention include compounds with a protecting group of the formula (II):

FTL-(X—CO.O—CH$_2$—Ph—NO$_2$)$_m$ (II)

where X is NH, O or S, m is an integer from 1 to 5 (e.g. 1, 2 or 3), Ph is an optionally substituted phenylene ring and FTL is a group such that FTL—(XH)$_m$ is a FTLi containing m —XH groups. The nitro group may be in the 2-position although is desirably in the 4-position of the ring relative to the Ph ring.

Within each compound of formula (II) where m from 2 to 5, each group X and Ph may be the same or different. Preferably, they are the same.

FTL inhibitors in formula (II) include those of formula (Ia), (Ib), or (Ic) above.

Suitable substituents of the phenylene ring include 1 to 4 groups which may be the same or different which are selected from fluorine, chlorine, bromine, iodine, hydroxy, mercapto, amino, nitro, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, and $C_{2-4}$ haloalkenyl. Preferably, the substituents are from 1 to 4 fluorines in the 2, 3, 5 and 6 positions of the ring.

Preferred prodrugs according to the invention are those of formula (IIIa):

FTL-(NH—CO.O—CH$_2$—Ph—NO$_2$)$_m$ (IIIa)

where m and Ph is as defined above and FTL is a group such that FTL-(NH$_2$)$_m$ is a FTLi compound containing m amino groups. Such prodrugs include those of formula (Ib) or (Ic) above which comprise at least one amino group. The nitro group may be in the 2-position although is desirably in the 4-position of the ring relative to the Ph ring.

Further preferred prodrugs of the invention are those of formula (IIIb):

FTL—(S—CO.O—CH$_2$—Ph—NO$_2$)$_m$ (IIIb)

where m and Ph is as defined above and FTL is a group such that FTL—(SH)$_m$ is a FTLi compound containing m mercapto groups. Such prodrugs include those of formula (Ib) or (Ic) above which comprise at least one mercapto group. The nitro group may be in the 2-position although is desirably in the 4-position of the ring relative to the Ph ring.

Preferred prodrugs of the invention are those of formula (IIIc):

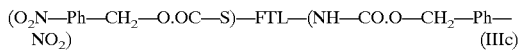

(O$_2$N—Ph—CH$_2$—O.OC—S)—FTL—(NH—CO.O—CH$_2$—Ph—NO$_2$) (IIIc)

wherein Ph which is the same or different is as defined above. FTL is a group such that (HS)—FTL—(NH$_2$) is a FTLi compound. Such prodrugs include those of formula (Ib) or (Ic) above. The nitro group may be in the 2-position although is desirably in the 4-position of the ring relative to the Ph ring.

Compounds of formulae (II) and (IIIa, b & c) may be used as prodrugs in an ADEPT or GDEPT system in conjunction with a nitroreductase enzyme, including the E.coli nitroreductase described in WO93/08288. While the present invention is not dependent, for its definition, upon the exact mode of action of the nitroreductase on the compound of formula II or (IIIa, b or c), it is believed that the nitro group of the p-nitrophenyl-benzyloxy-carbonyl residue is converted to the corresponding amino or hydroxylamino group and that the resulting p-aminobenzyloxycarbonyl or p-hydroxylaminobenzyloxycarbonyl compound automatically degrades under the reaction conditions used for the enzymatic reduction to release the cytotoxic compound and form p-aminobenzyl alcohol or p-hydroxylaminobenzyl alcohol and carbon dioxide as by products in accordance with the following reaction scheme:

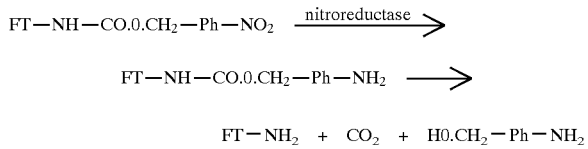

FT—NH—CO.0.CH$_2$—Ph—NO$_2$ $\xrightarrow{\text{nitroreductase}}$

FT—NH—CO.0.CH$_2$—Ph—NH$_2$ $\longrightarrow$

FT—NH$_2$ + CO$_2$ + HO.CH$_2$—Ph—NH$_2$

The p-nitrobenzyloxycarbonyl compounds of the invention are conveniently prepared by methods of chemical synthesis known per se. For example, suitably protected amine or hydroxy ras inhibitor compounds can be reacted with 4-nitrobenzyl chloroformate under anhydrous conditions in the presence of a hydrogen chloride acceptor, particularly an alkylamine such as triethylamine. This reaction can be carried out in a dry organic solvent such as chloroform and the resulting compound of the invention of formula II or formula IIIa, b or c isolated from the organic solvent by conventional methods such as chromatography. For use in ADEPT the prodrug should be unable to or have limited ability to enter cells, whereas for GDEPT the prodrug must enter cells. Accordingly, modifications may be made in the prodrug, eg in the benzene ring, to make the prodrug more, or less, lipophilic. The gamma acid of the glutamic acid may be altered to make compounds more lipophilic, eg with an ester group.

Similar prodrugs which can be activated by a carboxypeptidase enzyme such as carboxypeptidase G2 (CPG2) can be made using derivatives of the formula (IV):

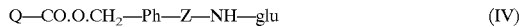

Q—CO.O.CH$_2$—Ph—Z—NH—glu (IV)

where Q is hydrogen or fluoro, chloro or bromo or —O— (N-succinimide), Ph is as defined above, Z is —O.CO— or —NH.CO— and glu is the residue of glutamic acid, ie a group:

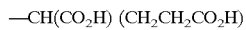

—CH(CO$_2$H) (CH$_2$CH$_2$CO$_2$H)

or a di-$C_{1-6}$ alkyl ester (e.g. an ethyl or t-butyl ester) thereof, in order to provide prodrugs of the formula (V):

FTL-(X—CO.O.CH$_2$—Ph—Z—NH—glu)$_m$ (V)

wherein X is as defined above and of the formula (VI)

FTL-(NH—CO.O.CH$_2$—Ph—Z—NH—glu)$_m$ (VI)

where FTL is the residue of a FTLi compound such that FTL-(XH)$_m$ and FTL-(NH$_2$)$_m$ are as defined above, and where m, Ph, Z and glu are also as defined above. As mentioned above in connection with prodrugs of formula (II) and formula (IIIa, b or c), for ADEPT the prodrug should have limited ability to enter cells whereas for GDEPT the prodrug may be modified if need be to make it more lipophilic in order that it does enter cells. The gamma carboxylic group of the glutamic acid may be altered to make compounds that are more lipophilic, e.g. with an aromatic or heterocyclic amide.

Within each compound of formula (V) where m from 2 to 5, each group X and Ph may be the same or different. Preferably, they are the same.

In compounds of formulae (IV), (V) and (VI), the group —Z— is in the 4-position of the ring relative to the FTL containing substituent.

Compounds of the formula (V) and (VI) in which the FTL is of formula (Ib) or (Ic) are preferred.

The benzyl chloroformate derivatives of the formula (IV) in which Z is —NH.CO— may be made from 4-(chloromethyl)phenyl isocyanate by reaction of glutamic acid or a protected derivative thereof, eg in which both carboxy groups of the glutamic acid residue are protected with ethyl or t-butyl groups. Suitably, the reaction is carried out in a solvent such as $CH_2Cl_2$ at about room temperature. The resulting intermediate, [4-chloromethyl]phenyl-uridoglutamate-di-tert-butylester, is treated in aqueous ethanol under reflux to provide the corresponding 4-hydroxymethyl compound and this is reacted with triphosgene (($CCl_3O)_2CO$) in an inert solvent, eg. THF, at room temperature to provide an optionally protected compound of formula (IV). The compound when protected may be deprotected by treatment with trifluoroacetic acid or formic acid.

The benzyl chloroformate derivatives of the formula (IV) in which Z is —O.CO— may be made starting from 4-hydroxybenzaldehyde in accordance with the reaction scheme in Scheme 1. Briefly, the aldehyde 5 is treated with 1,2-ethane dithiol in borane trifluoroetherate plus $CH_2Cl_2$ at 25° C. for about 12 hours to form the 1,3 dithiolane intermediate which is treated with triphosgene as above to form the 4[1,3 dithiolane] phenylchloroformate. This is coupled with ditertbutyl-glutamate hydrochloride in dry THF in the presence of triethylamine at room temperature for about 5 hours, to provide 4[1,3 dithiolane] phenylcarbamate-glutamate-di-t-butyl. The dithiolane is deprotected with mercuric perchloroate in methanol and cholorform at about 25° C. for about 5 minutes. The aldehyde is converted to the corresponding benzylic alcohol by mild reduction with sodium borohydride at room temperature in ether and then converted to the corresponding chloroformate with triphosgene as described above.

Preferred compounds of formula (IV) where Q is —O—(N-succinimide) are the novel compounds of formula (XVI):

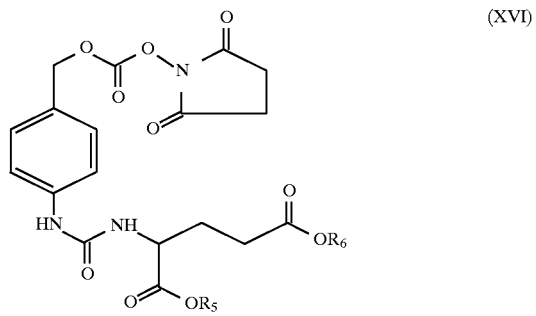

(XVI)

wherein $R_5$ represents $C_{1-6}$ alkyl, preferably ethyl or t-butyl. Therefore, according to a further aspect of the present invention there is provided compounds of formula (XVI). These compounds may be prepared according to the method disclosed in Example 2 or analogous methods.

SCHEME 1

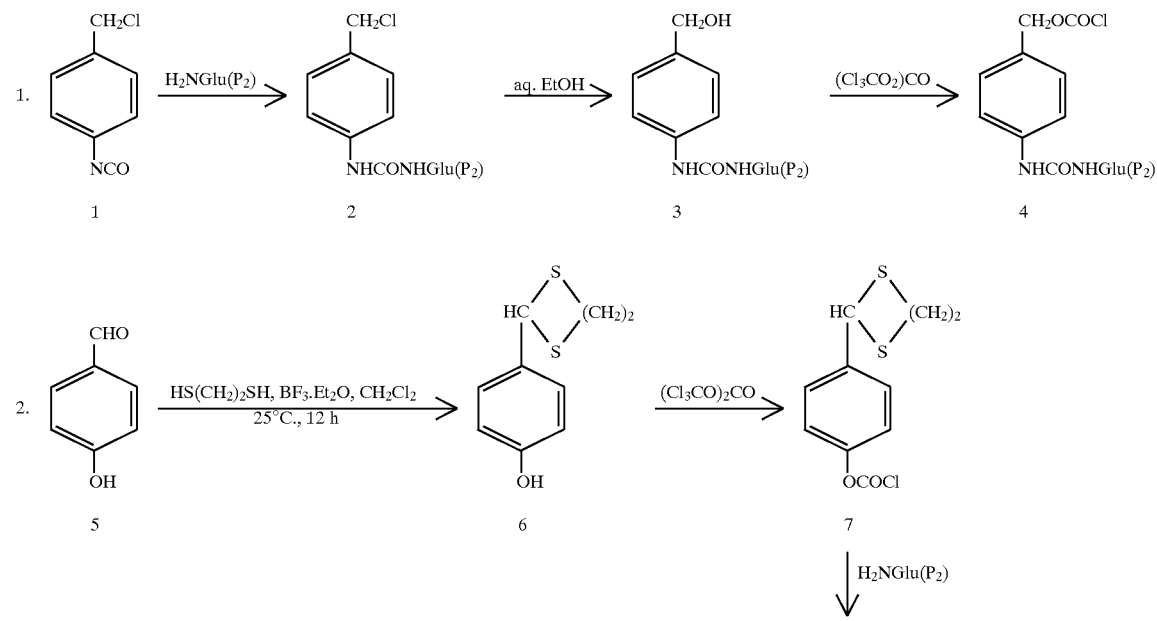

-continued
SCHEME 1

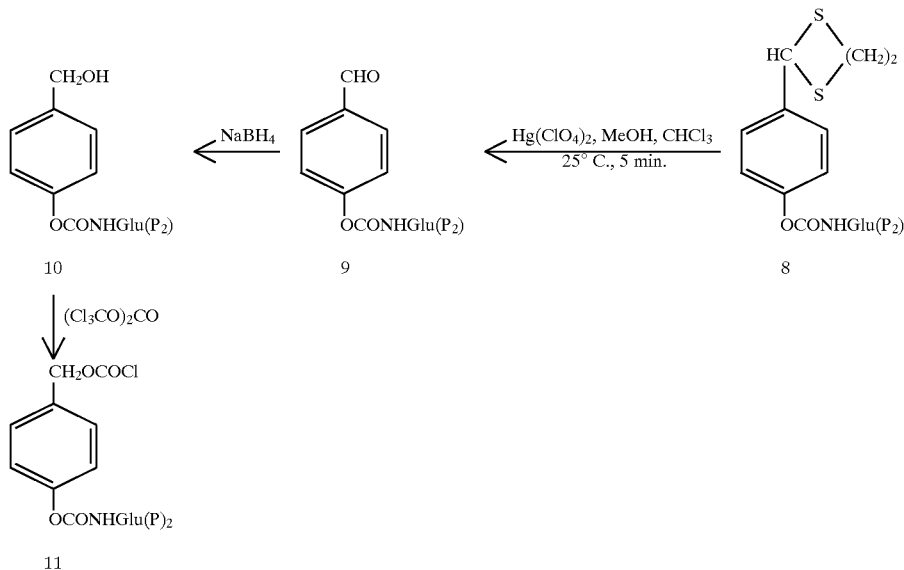

Compounds of the formula (V) and (VI) may be made from ras inhibitors which contain an amino or hydroxy group by analogous procedures to the methods described above for the production of compounds of formulae (II) and (III).

Ras inhibitor prodrugs of the formulae (V) or (VI) will be activated by carboxypeptidases such as CPG2 by the action of the enzyme to remove the glutamic acid residue followed by "self immolation" of the remaining prodrug in a manner analogous to that described above in relation to the nitroreductases.

Prodrugs of the formula (V) where Z is —NH.CO— may also be made using linkers of the formula (VII):

$$HOH_2C-Ph-NH-CO-NH-glu \quad (VII)$$

where Ph and glu are as defined above. The optionally substituted phenylene group is substituted at the 4-position by the glu-containing moiety relative to the hydroxymethyl group.

The linkers of formula (VII) may be made from optionally substituted 4-nitrobenzyl alcohol, where the optional substituents are as defined for the group —Ph— above. The hydroxyl group of the 4-nitrobenzyl alcohol is protected, for example by reaction with tert-butyl-diphenyl-chloro-silane at room temperature in an organic solvent, to provide an optionally substituted (4-nitro-benzyl) tert-butyl-di-phenyl-silyl ether. The 4-nitro group is then reduced to an amine group by catalytic hydrogenation or catalytic hydrogen transfer, for example with ammonium formate in the presence of a catalyst such as Pd/C in a protic solvent such as an alcohol, e.g. methanol or ethanol.

The amine group may then be converted into an isocyanate group for example by reaction with phosgene, diphosgene or triphosgene in the presence of a tertiary organic amine such as triethylamine and an aprotic organic solvent with a boiling point higher than 50° C. such as toluene. The isocyanate compound is then reacted with di-$C_{1-6}$alkyl-glutamic acid or derivative thereof, eg di-$C_{1-6}$alkyl-glutamate hydrochloride. This may be done at room temperature in the presence of triethylamine in an aprotic organic solvent such as toluene, THF or dichloromethane.

Alternatively, the amine compound may be reacted directly in a one-pot synthesis with the di-$C_{1-6}$alkyl-glutamic acid or derivative thereof in the presence of triphosgene and triethylamine in an aprotic solvent such as THF or dichloromethane.

In either case, the resulting compound is treated to remove the hydroxy-protecting group, for example by the use of tetra-butyl-ammonium fluoride in THF at room temperature.

The resulting compound of formula (VII) where glu is in the form of a di-$C_{1-6}$alkyl ester may be deprotected to remove the ester groups for example by the use of an acid such as formic or trifluoro acetic acid. Compounds of formula (VII) or (XVI) may be linked to a FTLi containing a group —OH, —$NH_2$ or —SH by reaction with the FTLi or activated derivative thereof in aprotic solvents such as dichloromethane and/or THF in the presence of a tertiary organic base such as triethylamine at room temperature, to provide a compound of the formula (V). The di-$C_{1-6}$alkyl ester groups of the compound, if present, may be removed as described above.

In order to link a FTLi with a group —XH to the linker of formula (VII) the group —XH may be converted to a reactive chloroformyl, chlorothioformyl or isocyanate derivative by the use of phosgene, diphosgene or triphosgene in the presence of a phase transfer catalyst such as tetra-butyl ammonium hydrogen sulphate. The reaction may be carried out in the presence of a base such as NaOH in an organic solvent such as toluene, THF or dichloromethane.

Prodrugs of the formula (V) in which Z is —O.CO— may be made using linkers of the formula (VIII):

$$HOH_2C-Ph-O-CO-NH-glu \quad (VIII)$$

where Ph and glu are as defined above. The optionally substituted phenylene group is substituted at the 4-position by the glu-containing moiety relative to the hydroxymethyl group.

To produce a compound of formula (VIII), optionally substituted 4-hydroxybenzaldehyde is protected as a 1,3-dithiane or dithiolanein in an aprotic solvent such as $CH_2Cl_2$ in the presence of $BF_3.Et_2O$, at room temperature by reaction with 1,3-propanedithiol or 1,2-ethanedithiol, to give the corresponding 4(1',3'-dithianyl) phenol or 4(1',3'-dithidanyl) phenol. This compound is coupled with di-$C_{1-6}$alkyl-glutamyl isocyanate, in an aprotic solvent such as toluene in the presence of a tertiary organic amine such as triethylamine, to the corresponding O[4(1',3'-dithianyl)-phenyl]N(di-$C_{1-6}$alkyl-glutamyl)carbamate. The deprotection of the carbamate to the corresponding aldehyde, may be carried out with $Hg(ClO_4)_2$ or $Tl(NO_3)_3$ in THF or dichloromethane at room temperature. The reduction of the aldehyde yields the desired O(4-benzyl-oxy)N(di-$C_{1-6}$alkyl-glutamyl) carbamate. This may be deprotected by treatment with an acid such as trifluoroacetic or formic acid to remove the alkyl ester protecting groups to provide a prodrug of formula (V).

The linkers of formula (VIII) may be attached to FTLi compounds containing a free hydroxy, amino or mercapto group in the same way as described above for the linkers of formula (VII) or (XVI).

Other suitable FTLi prodrugs include those which are derivatized with a sugar or a β-lactam derivative. For example, suitable linkers which may be attached to FTL inhibitors of the type FTL—$NH_2$ or FTL—OH or FTL—SH described above are:

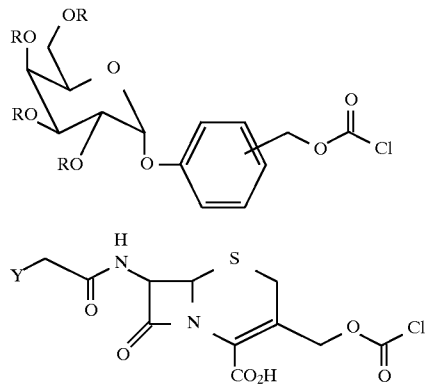

where R is hydrogen or acetyl and Y is aryl such as phenyl, benzyl or tolulyl, and these may be made in an analogous manner to the other prodrugs described above.

Any hydroxy, amino or mercapto group of a FTLi may be linked in the manner described above to provide a prodrug of the present invention. If desired, more than one such group may be derivatized to make a prodrug. If however only a single hydroxy, mercapto or amino group is to be reacted to form a prodrug, any remaining groups of the FTL may be protected with for example t-butyl or adamantyl groups (in the case of hydroxyl) or butyloxycarbonyl groups in the case of amino. Such protecting groups may be attached using chemical processes known in the art. The groups of the FTLi to be reacted with the linker may be derivatized to the corresponding haloformate or isocyanate and then coupled with the linkers such as those of formulae (VII) or (VIII). After the FTLi prodrug has been made, the protecting groups may be removed by conventional means, eg by treatment with trifluoroacetic acid.

Physiologically acceptable derivatives of said prodrug include salts, amides, esters and salts of esters. Esters include carboxylic acid esters in which the non-carbonyl moiety of the ester grouping is selected from straight or branched chain $C_{1-6}$alkyl, (methyl, n-propyl,, n-butyl or t-butyl); or $C_{3-6}$cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. Other salts include acid addition salts, including the hydrochloride and acetate salts. Amides include non-substituted and mono- and di-substituted derivatives.

The invention further provides pharmaceutical formulations. Such formulations comprise a compound of the invention together with one or more pharmaceutically acceptable carriers or diluents.

Pharmaceutically acceptable carriers or diluents include those used in formulations suitable for oral or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Suitable liposomes include, for example, those comprising the positively charged lipid (N[1-(2,3-dioleyloxy) propyl]-N,N,N-triethylammonium (DOTMA), those comprising dioleoylphosphatidylethanolamine (DOPE), and those comprising 3β[N-(n',N'-dimethylaminoethane)-carbamoyl]cholesterol (DC-Chol).

The ras inhibitor prodrugs of the present invention and the antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour and the premature release of the ras inhibitor agent is minimised.

In GDEPT the prodrug will usually be administered following administration of the modifed virus encoding an enzyme. Typically, the virus will be administered to the patient and then the uptake of the virus by infected cells monitored, for example by recovery and analysis of a biopsy sample of targeted tissue. Alternatively, the prodrug may be administered following the administration of a delivery system containing the gene encoding the enzyme.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

The exact dosage regime for both GDEPT and ADEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and either the enzyme/agent conjugate or modified virus and administration by the intravenous route is frequently found to be the most practical. In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from 5 to 2000 mg/m$^2$ (e.g. 200 mg/m$^2$).

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

In GDEPT systems, the amount of virus or other vector delivered will be such as to provide a similar cellular concentration of enzyme as in the ADEPT system mentioned above. This may be determined by clinical trials which involve administering a range of trial doses to a patient and measuring the degree of infection or transfection of a target cell or tumour. The amount of prodrug required will be similar to or greater than that for ADEPT systems.

The present invention also provides a system for use in the control of neoplasia in a human or animal subject comprising an enzyme capable of converting a ras inhibitor prodrug to an active ras inhibitor, preferably conjugated with a targeting agent such as monoclonal antibody that will bind to a tumour-associated antigen, in association with a ras inhibitor prodrug as defined above. When the enzyme is a nitroreductase, the system also preferably comprises a suitable cofactor for the enzyme. Suitable cofactors include a riboside or ribotide of nicotinic acid or nicotinamide.

The present invention extends to a method of treating neoplasia in a human or animal subject requiring such treatment which comprises administering to the host an effective amount of a ras inhibitor prodrug of the invention and an enzyme, preferably conjugated with a targeting agent such as a monoclonal antibody that will bind to a tumour-associated antigen. Tumour-associated antigens include tumour-associated receptors present on the cell surface.

The present invention also provides a system for use in the control of neoplasia in a human or animal subject comprising a modified virus capable of selectively infecting tumour cells in said subject, said virus carrying a DNA or RNA sequence encoding an enzyme, in association with a ras inhibitor prodrug capable of being converted to a ras inhibitor by the action of said enzyme.

The present invention extends to a method of treating neoplasia in a human or animal subject requiring such treatment which comprises administering to the host an effective amount of a ras inhibitor prodrug of the invention and a modified virus, said modified virus capable of selectively infecting tumour cells in said subject, said virus carrying a DNA or RNA sequence encoding an enzyme capable of converting said ras inhibitor prodrug to a ras inhibitor.

The present invention also extends to a method of treating neoplasia in a human or animal subject requiring such treatment which comprises administering to the host an effective amount of a ras inhibitor prodrug of the invention and a non viral vector system, said non-viral vector system capable of being selectively introduced into tumour cells in said subject, said vector system carrying a DNA or RNA sequence encoding an enzyme capable of converting said ras inhibitor prodrug to an active ras inhibitor operably linked to a promoter effective in expressing said enzyme in said cells.

The various systems for use in the treatment of neoplasia by ADEPT described above optionally include the "second component" for accelerated clearance described above. Likewise, the methods of treatment of neoplasia described above optionally include as part of that method the use of the second component, an effective amount of which is administered after administration of the enzyme, in order to increase the ratio of localised to freely circulating enzyme. Reference may be made to WO89/10140 for further particular details of the second component, and such details can be incorporated for use in the present invention.

Modified viruses capable of selectively infecting tumour cells are known in the art. By "selectively infecting" it is meant that the virus will primarily infect tumour cells and that the proportion of non-tumour cells infected is such that the damage to non-tumour cells by administration of the ras inhibitor prodrug will be acceptably low, given the nature of the disease being treated. Ultimately, this will be determined by the physician.

It will also be understood that the DNA or RNA sequence encoding an enzyme carried by the virus will be linked to suitable expression control signals such that expression of the enzyme will occur in the targeted tumour cells.

The non-viral vector system will be capable of being selectively introduced into tumour cells utilizing methods such as those mentioned above, e.g. calcium phosphate co-precipitation, microinjection, liposomes, direct DNA uptake, and receptor-mediated DNA transfer (Morgan & French Anderson, Annu. Rev. Biochem., 1993,62;191).

Suitable monoclonal antibodies for use in the present invention include antibodies to cerbB2, such as ICR12 (Bakir, M A et al, J. Nucl. Med (1992) 33;2154–2160), and antibodies to epidermal growth factor receptor, such as ICR16 (Dean, C J et al, Int. J. Cancer Suppl. 8,(1994), 103). Evidence that cerbB2 requires ras for transformation is given in Ben-Levy et al, Embo J.13,3302,1994.

As used herein, the term "monoclonal antibody" will be understood by those of skill in the art not simply to refer to antibodies produced by traditional hybridoma techniques, but also to cover antibodies and variants thereof produced by recombinant means. These include, for example, humanised antibodies such as those with a constant region from a human antibody grafted onto a non-human antibody variable region (see for example EP-A-O 120 694), chimeric antibodies such as those with non-human complementarity determining regions (CDRs) grafted into a human variable region framework (see for example EP-A-O 239 400) and single chain antibodies. Fragments of such monoclonal antibodies which retain their target binding activity are also included by the general term "monoclonal antibody". This includes Fv, Fab' and F(ab')$_2$ fragments. It also includes recombinant or synthetic proteins based upon the CDRs of such antibodies, e.g. abzymes (a polypeptide with both antibody-like binding acitivity and enzyme activity) and diabodies.

Prodrugs of the present invention may also be used as reagents in in vitro systems to test the activity of candidate enzymes or antibodies which may be incorporated into ADEPT or GDEPT systems.

For example, a tumour cell line carrying a marker to which an antibody is directed may be grown in vitro, and then an antibody-enzyme conjugate added to the culture. The enzyme will be one which is, or suspected to be, capable of converting a prodrug of the invention into an active drug. The prodrug is then added to the culture and the amount of cell killing or inhibition of cell growth is measured (for example by using a vital stain to record the number of viable cells or by replating a sample of the culture to count the number of viable cells).

EXAMPLES

The following Examples 1 and 2 further illustrate the invention. Preparative example 1 is an illustration of the preparation of a compound of formula (Ib). The reaction schemes which follow further illustrate the Examples.

All starting materials, reagents and anhydrous solvents (THF under N$_2$) were purchased from Aldrich, unless otherwise stated. TLC was performed on precoated sheets of Kiselgel 60 F$_{254}$ (Art 5735, Merck). Preparative TLC was carried out on Silica Gel plates (20×20 cm) from Analtech. NMR spectra were determined in Me$_2$SO-d$_6$ on a Brucker AC250 spectrometer (250 MHz) at 30° C. (303K) unless otherwise stated. Coupling constants (J) were expressed in Hz.

PREPARATIVE EXAMPLE 1

N-methoxy-N-methyl Amide of N-t-butoxycarbonyl Isoleucine (I)

O,N,-Dimethylhydroxylamine hydrochloride (976 mg, 10 mmol) was suspended in dichloromethane (10 ml) and cooled to −10° C. 1-methylpiperidine (992 mg, 1.22 ml, 10 mmol) was then added slowly, keeping the temperature below −2° C. This solution was stored at −10° C. In a separate flask N-boc isoleucine (2.290 g, 9.9 mmol) was dissolved in dichloromethane (40 ml) and cooled to −20° C. 1-methylpiperidine (992 mg, 1.22 ml, 10 mmol) and isobutylchloroformate (1.336 g, 1.30 ml, 10 mmol) were then added keeping the temperature below −20° C. After 15 min the hydroxylamine solution prepared above was added in a single portion and the solution stirred at ambient temperature overnight. The solution was then washed with saturated ammonium chloride solution (2×30 ml), dried over magnesium sulfate, filtered and the solvent removed under reduced pressure to yield a yellow oil which was purified by column chromatography (silica —10–30% ethylacetate in hexane) to yield the N-methoxy-N-methyl amide (2.28 g, 84%) as a colourless oil.

The yields for the subsequent preparations of this compound varied between 60 and 84%.

N-t-Butoxycarbonyl isoleucinal (2)

The Weinreb amide of N-t-butoxycarbonylisoleucine, prepared above, (1.98 g, 7.2 mmol) was dissolved in anhydrous ether (10 ml) and cooled to −45° C. Lithium aluminium hydride (10 ml of a 1N solution in ether, 10 mmol) was then added keeping the temperature below −35° C., after addition the solution was then allowed to warm to 5° C. The solution was then cooled to −45° C. and sodium sulfate decahydrate (5.00 g) added and the cooling bath removed. After 1 hour the solution was filtered through celite and the solvent removed under reduced pressure to yield the aldehyde (1.47 g, 95%) as a colourless oil, which was immediately used in the next reaction as it racemises at room temperature.

The yields for the subsequent preparations of this compound varied between 89 and 97%.

N-[2(S)-[t-butoxycarbonylamino]-3-methylpentyl]-isoleucine (3)

Isoleucine (1.31 g, 9.95 mmol) was suspended in anhydrous methanol (10 ml) and trifluoroacetic acid (1.133 g, 0.77 ml, 9.95 mmol) was added. The mixture was stirred until all the isoleucine had dissolved and the solvent was then removed under reduced pressure. Anhydrous DMF (10 ml) was added to the resulting isoleucine trifluoroacetate salt followed by 3 Å molecular sieves and a solution of 2 (1.47 g, 4.9 mmol) in anhydrous DMF (5 ml). After 15 minutes the solution was treated with sodium triacetoxy borohydride (1.58 g, 7.45 mmol) and stirred overnight. The resulting suspension was filtered through celite, diluted with ethyl acetate (50 ml) and washed with saturated sodium chloride solution (2×35 ml). The organic extracts were dried over magnesium sulfate, filtered, and the solvent removed under reduced pressure to yield the acid (1.36 g, 84%) as a yellow oil.

The yields for the subsequent preparations of this compound varied between 67 and 88%.

N-2(S)-[t-butoxycarbonylamino-3-methylpentyl]-isoleucylhomoserine lactone (4)

Compound 3 (331 mg, 1 mmol), dissolved in anhydrous DMF (2 ml) was treated with hydroxybenzotriazole hydrate (135 mg, 1 mmol), 1-(3-dimethylaminopropyl)-3-ethyl carbodiimide hydrochloride (260 mg, 1.36 mmol) and homoserine lactone hydrochloride (125 mg, 1 mmol). Triethylamine (174 mg, 0.24 ml, 1.72 mmol) was added and the mixture stirred overnight. The solution was diluted with ethyl acetate (25 ml) and washed with saturated sodium chloride solution (2×10 ml), dried over magnesium sulfate, filtered and the solvent removed under reduced pressure to yield a yellow oil. This was then purified by column chromatography (5% methanol in dichloromethane) and by precipitation from ether by the dropwise addition of hexane, to give the product as a white powder (147 mg, 47%).

The yields for the subsequent preparations of this compound varied between 41 and 54%; m/z: [M+H]$^+$=414; microanalysis data:

|   | Expected % | Found % |
|---|---|---|
| C | 60.99 | 60.7 |
| H | 9.51 | 9.8 |
| N | 10.16 | 9.9 |

N-[2(S)-Amino-3-methylpentyl]-isoleucylhomoserine lactone hydrochloride (5)

Compound 4 (147 mg, 0.35 mmol) was dissolved in ethyl acetate (10 ml) and cooled to −25° C. Anhydrous hydrogen chloride gas was then passed through the solution until tlc (5% methanol in dichloromethane) showed complete reaction. Nitrogen was then passed through the solution to remove excess hydrogen chloride. The solvent was then removed under reduced pressure to yield the product as a pale yellow solid (125 mg, 91%).

The yields for the subsequent preparations of this compound varied between 62 and 92%.

N-methoxy-N-methyl amide Of N-t-Butoxycarbonyl-S-Trityl-cysteine (6)

O,N-dimethylhydroxylamine hydrochloride (108 mg, 1.1 mmol) was suspended in dichloromethane (10 ml) and cooled to −10° C. 1-methylpiperidine (110 mg, 0.13 ml, 1.1 mmol) was then added slowly, keeping the temperature below −2° C. This solution was stored at −10° C. In a separate flask N-boc-S-trityl cysteine (464 mg, 1 mmol) was dissolved in dichloromethane (20 ml) and cooled to −20° C. 1-methylpiperidine (110 mg, 0.13 ml, 1.1 mmol) and isobutylchloroformate (144 mg, 0.14 ml, 1.1 mmol) were then added keeping the temperature below −20° C. After 15 min the hydroxylamine solution prepared above was added in a single portion and the solution stirred at ambient temperature overnight. The solution was then washed with saturated ammonium chloride solution (2×15 cm$^3$), dried over magnesium sulfate, filtered and the solvent removed under reduced pressure to yield a white foam which was purified by column chromatography (silica —10–30% ethyl acetate in hexane) to yield the N-methoxy-N-methyl amide (406 mg, 81%) as a white foam.

The yields for the subsequent preparations of this compound varied between 81 and 92%.

N-t-butoxycarbonyl-S-trityl-Cysteinal (7)

The Weinreb amide of N-t-butoxycarbonyl-S-tritylcysteine, prepared above, (406 mg, 0.8 mmol) was dissolved in anhydrous ether (5 ml) and cooled to −45° C. Lithium aluminium hydride (1 ml of a 1N solution in ether, 1 mmol) was then added keeping the temperature below −35° C., after addition the solution was then allowed to warm to 5° C. The solution was then cooled to −45° C. and sodium sulfate decahydrate (1.25 g) added and the cooling bath removed. After 1 hour the solution was filtered through celite and the solvent removed under reduced pressure to yield the aldehyde (332 mg, 93%) as a white foam.

The yields for the subsequent preparations of this compound varied between 84 and 93%.

N-[2(S)-2-{(t-butoxycarbonyl)amino)-3-[(triphenylmethyl)thio]propyl]amino[-3-methylpentyl]isoleucylhomoserine lactone (8).

Compound 5(125 mg, 0.32 mmol) was dissolved in anhydrous methanol (10 ml) and treated with 3 Å molecular sieves, potassium acetate (64 mg, 0.64 mmol), N-t-butoxycarbonyl-S-trityl cysteinal (289 mg, 0.64 mmol) and sodium cyanoborohydride (31 mg, 0.48 mmol). The mixture was stirred at ambient temperature for 24 hours, filtered through celite and the methanol removed under reduced pressure. The residue was dissolved in ethyl acetate (25 ml), washed with saturated ammonium chloride solution (15 ml) and saturated sodium chloride solution (15 ml), dried over magnesium sulfate, filtered and the solvent removed under reduced pressure to yield a white foam. This was then purified by column chromatography (silica, 1–3% methanol in dichloromethane) to yield the desired compound (107 mg, 45%) as a white foam.

The yields for the subsequent preparations of this compound were 32 and 43%; m/z:[M+H]$^+$=745.

EXAMPLE 1

SUMMARY

Two ras inhibitor prodrugs which may be activated by nitroreductase were made. These are N-{2(R)-[[2(4'-nitrobenzyloxy-carbonyl)-amino-3-mercaptopropyl]amino]-3-methyl-pentyl]isoleucylhomoserine lactone, 10 and N{2(R)-[[2(4'-nitrobenzyloxy-carbonyl)-amino)-3[(4'-nitrobenzyloxy-carbonyl)-thio]propyl]amino]-3-methyl-pentyl]isoleucylhomoserine lactone, 11 (see scheme 2). The starting material was N-{2(S)-2-[(tertbutoxy-carbonyl)-amino-3[(triphenylmethyl)thio]propyl]amino]-3-methyl-pentyl]isoleucylhomoserine lactone, 8, which was the product of Preparative Example 1. It was deprotected by using triethylsilane and TFA in CH$_2$Cl$_2$ (according to Graham et al. (J. Med. Chem., 1994, 37(6), 725–732) procedure with the sole difference that the reaction was carried out at 4° C.). After work up (but no final purification by HPLC), the compound 9, thus obtained was reacted with 4-nitro-benzyl chloroformate to give a mixture of compounds 10 and 11 which were separated and purified by preparative TLC. The disappearance from the 1H-NMR spectrum of compound 11, of the proton belonging to the mercapto group (range 1.0–2.0 ppm) supported the location of the second nitrobenzylic moiety.

SCHEME 2

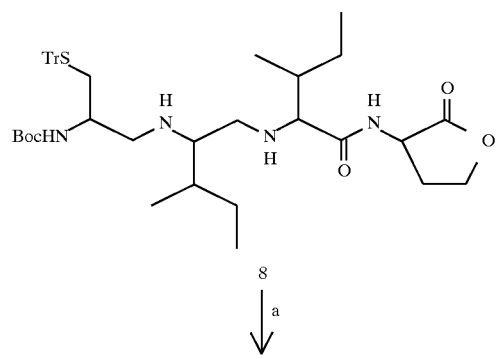

8

↓a

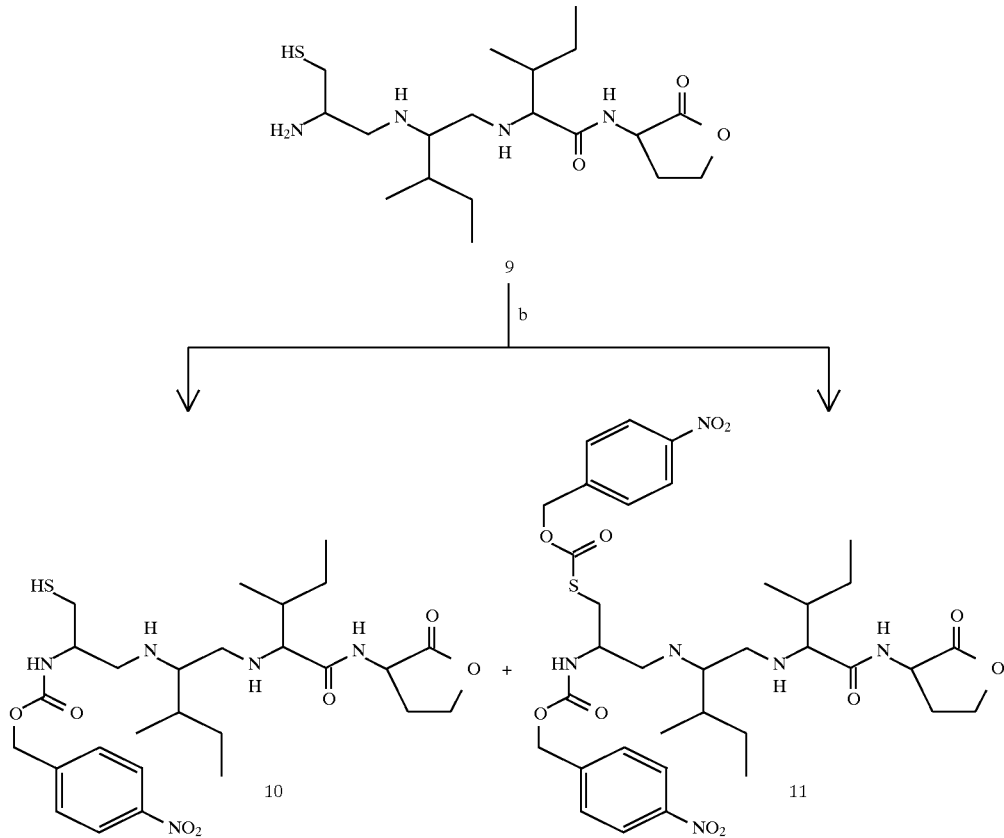

N-{2(R)-[2(-amino-3-mercaptopropyl)amino]-3-methyl-pentyl]isoleucylhomoserine lactone 9

N-{2(S)-2-[tertbutoxycarbonyl)amino3[(triphenylmethyl)-thio]propyl]amino]3-methyl-pentyl] isoleucylhomoserine lactone, 8, (0.200 g, 0.148 mmol) was dissolved in $CH_2Cl_2$ (2.0 ml) with TFA (1.0 ml) and triethylsilane (0.18 ml, 0.13 g, 1.1 mmol) at 4° C. The mixture was stirred at this temperature for 2 h, then allowed to reach the ambient temperature and concentrated to dryness. The residue was partitioned between hexane fraction and aqueous TFA 0.1% (6.0 ml). The aqueous layer was washed with hexane fraction (2×2.5 ml), filtered and concentrated to dryness at 20°–25° C. An oily residue (0.257 g) was obtained which was used without further purification.
N-{2(R)-[[2(4'-nitro-benzyloxy-carbonyl)-amino-3-mercaptopropyl]amino]-3-methyl-pentyl] isoleucylhomoserine lactone, (10) and N-{2(R)-[[2(4'-nitro-benzyloxy-carbonyl)-amino]-3[(4'-nitro-benzyloxy-carbonyl)-thio]propyl]amino]-3-methyl-pentyl]isoleucylhomo serine lactone 11

To a stirred solution of the previous lactone product, 9, (0.128 g) in THF (dry) (2 ml) and triethylamine (0.12 ml, 0.081 g, 0.8 mmol), was added 4-nitro-benzyl chloroformate (0.047 g, 0.22 mmol). After 5 h, the reaction mixture was evaporated to an oil (0.175 g). The oil was partitioned between EtOAc (3 ml) and $H_2O$ (2 ml). The organic layer was washed with $H_2O$ (2×2 ml), dried ($MgSO_4$) and evaporated under vacuum. An oil (0.070 g) resulted containing a mixture of 10 and 11. The compounds were purified by preparative TLC. Eluent: EtOAc: cyclohexane 3:1. 10 eluted first: 0.005 g yield=33%. $^1$H-NMR, $d_H$: 0.73–0.90 (12H, m), 1.00–1.22 (3H, m, 2H+$H_s$), 1.25 (2H, d, J=7.44), 1.40–1.52 (3H, m), 2.10–2.18 (1H, m), 2.30–2.82 (5H, m), 2.90–3.10 (1H, m), 4.00–4.10 (1H, m), 4.15–4.27 (1H, m), 4.30–4.42 (1H, m), 4.50–4.65 (1H, m), 5.40 (2H, s, $CH_2$-benzyl), 7.63 (2H, d, J=8.70, $H_{arom2+6}$), 8.24 (2H, d, $H_{arom3+5}$); $C_{27}H_{43}N_5O_7S$.

11 eluted later: 0.003 g yield=15%. $^1$H-NMR, $d_H$: 0.70–0.92 (12H, m), 1.03–1.20 (2H, m), 1.25 (2H, d, J=6.12), 1.40–1.60 (3H, m), 2.16–2.24 (1H, m), 2.25–2.82 (5H, m), 2.82–2.92 (1H, m), 3.64–3.80 (1H, m), 4.12–4.26 (1H, m), 4.27–4.43 (1H, m), 4.50–4.65 (1H, m), 5.16 (2H, s, $CH_2$—S-benzyl), 5.39 (2H, s, $CH_2$—N-benzyl), 7.59 (2H, d, J=8.30, $H_{arom2+6}$, S—$PhNO_2$), 7.61 (2H, d, J=8.46, $H_{arom2+6}$, N—$PhNO_2$), 8.20 (2H, d, $H_{arom3+5}$, S—$PhNO_2$), 8.21 (2H, d, $H_{arom3+5}$, N—$PhNO_2$); $C_{35}H_{48}N_6O_{11}S$.

EXAMPLE 2

SUMMARY

For the synthesis of a novel ras prodrug cleavable by the enzyme CPG2, an ester of a self-immolative linker was designed to be coupled to mercapto or amino functional groups. This is: $N^1$ (4'-succinimidyl-oxycarbonyl-oxybenzyl)$N^3$(di-tert-butyl-glutamyl) urea, 20 (see scheme 3). Once coupled to the ras inhibitor, the ester protecting groups are removed. The route to the ras prodrug is exemplified.

The intermediate $N^1$(4-hydroxybenzyl)$N^3$ (di-tert-butyl-glutamyl) urea 19, was synthesised for coupling to ras inhibitor drugs according to the Scheme 2. The starting material, 4-nitrobenzylic alcohol, 12, was protected as tertbutyl-di-phenyl-silyl ether, 13, by reacting with tert-butyl-diphenyl-chlorosilane and imidazole in DMF (or THF) at room temperature. The protected nitro derivative, 13, was reduced by hydrogen transfer with ammonium formate (Pd/C 10% in EtOH). The amine, 14, thus formed was reacted with triphosgene in toluene at 70° C., to form the corresponding isocyanate 15. The protected linker, 18, was obtained by coupling the isocyanate 15 with di-tert-butyl-glutamate in THF in the presence of NEt₃ at room temperature. An alternative route to 18 was by the direct coupling of amine 14 with the di-tert-butyl-glutamyl isocyanate 17, under the same conditions as described above, where the di-tert-butyl-glutamyl isocyanate 17 was obtained from the di-tert-butyl-glutamate by treatment with triphosgene and NEt₃ in toluene at −78° C. Using this route, the compound 18 was obtained in good yield from the amine 14 and di-tert-butyl-glutamate in a one-pot synthesis.

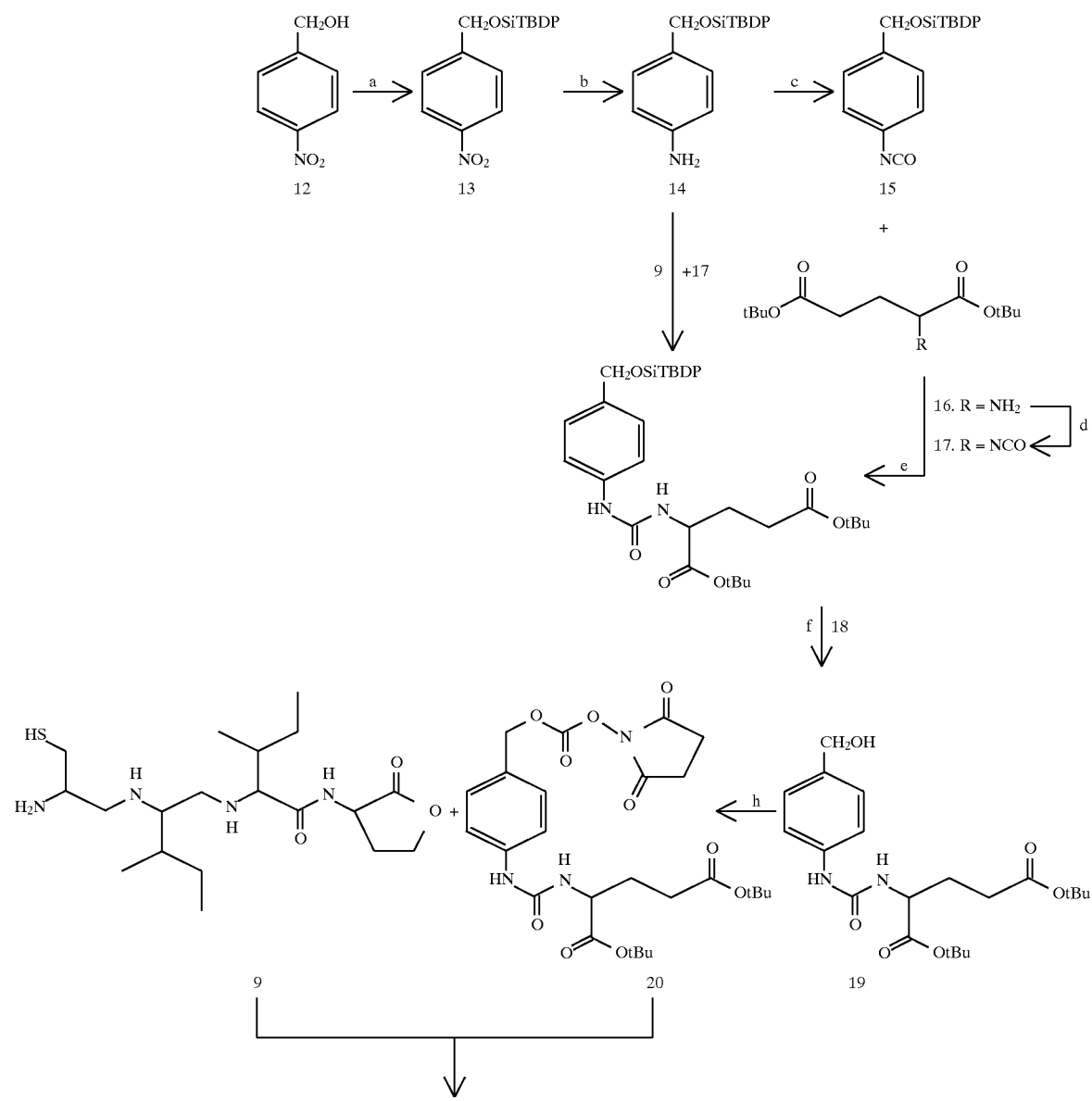

SCHEME 3
Bas linker for CPG-2)

-continued
SCHEME 3
Bas linker for CPG-2)

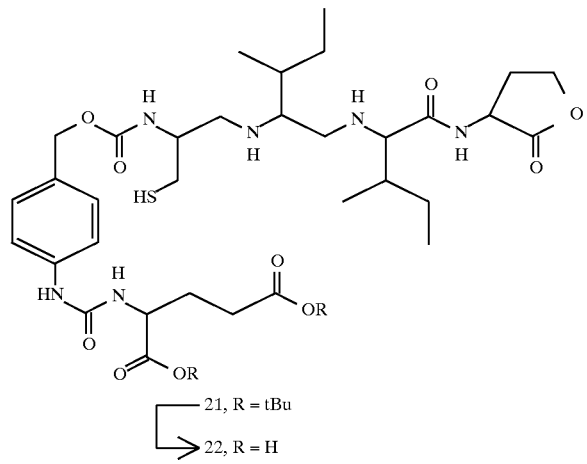

21, R = tBu
22, R = H

The compound 18 was deprotected by Bu$_4$NF in THF at room temperature and the di-tert-butyl ester of the linker, 19, was purified by column chromatography. The compound 19 was reacted with the disuccinimidyl carbonate in acetonitrile and triethylamine at room temperature leading to the desired succinimidyl linker, 20. This is then coupled with the ras inhibitor, 9 (prepared according to Preparative Example 1 and Example 1), giving the compound, 21, which is then deprotected in formic acid at 4° C. to give the final ras prodrug, 22.

EXPERIMENTAL (4-nitro-benzyl) tert-butyl-di-phenyl-silyl ether (13).

To a stirred solution of 4-nitrobenzyl alcohol, 12, (1.00 g, 6.50 mmol), and imidazole (0.97 g, 14.1 mmol) in DMF (10.0 ml), was added tert-butyl-diphenyl-chlorosilane (1.98 g, 7.20 mmol) over 10 min under N$_2$ at room temperature. The reaction mixture was stirred for an additional 5 h, diluted with Et$_2$O (75 ml), washed with H$_2$O (5×15 ml), dried (MgSO$_4$) and evaporated to dryness under vacuum. An oil was obtained which crystallised on standing and was recrystallised to a solid from EtOH (70%); yield: 2.36 g (93%). $v_{max}$/cm$^{-1}$ (film): 2931, 2857 (CH$_2$, asym., sym.), 1521, 1345 (NO$_2$); $^1$H-NMR, d$_H$: 1.06(9H, s, t-Bu), 4.92 (2H, s, CH$_2$), 7.42–7.46 (5H, m, Ph), 7.63–7.65 (7H, m, Ph+H$_{arom2+6}$), 8.23 (2H, d, J=8.23, H$_{arom3+5}$); MS, (EI), (391.54); m/z: 334 (M - t-Bu, 100), 288 (M - t-Bu - NO$_2$, 10), 256 (M - t-Bu - Ph, 20), 199 (Ph$_2$SiOH$^+$, 100); C$_{23}$H$_{25}$NO$_3$Si.

(4-amino-benzyl) tert-butyl-di-phenyl-silyl ether (14)

To a stirred solution of 13 (5.00 g, 12.77 mmol) in ethanol (100 ml) was added Pd/C (10%, 1.50 g) and ammonium formate (4.60 g) at room temperature. After 1.5 h the catalyst was removed by filtration, the filtrate concentrated to dryness under vacuum and the residue partitioned between EtOAc:H$_2$O. The organic layer was dried (MgSO$_4$) and concentrated under vacuum to give 14 as an oil; yield: 4.24 g (92%); $v_{max}$/cm$^{-1}$ (film): 3433, 3378 (NH$_2$), 2931, 2857 (CH$_2$, asym., sym.); $^1$H-NMR, d$_H$: 1.00 (9H, s, t-Bu), 4.57 (2H, s, CH$_2$), 4.98 (2H, s broad, NH$_2$), 6.52 (2H, d, J=8.25, H$_{arom3+5}$), 6.96 (2H, d, H$_{arom2+6}$), 7.42–7.46 (5H, m, Ph), 7.62–7.65 (5H, m, Ph); MS, (EI), (361.56); m/z: 361 (M$^+$, 8), 304 (M - t-Bu, 100), 199 (Ph$_2$SiOH$^+$, 100); C$_{23}$H$_{27}$NOSi.

(4-isocyanato-benzyl)tert-butyl-di-phenyl-silyl ether (15)

To a stirred solution of 14 (0.63 g, 1.70 mmol) and triethylamine (0.16 g, 0.60 mmol) in toluene (10 ml) at 70° C., was added triphosgene (0.18 g, 1.7 mmol). After 5 h the reaction mixture was filtered and the filtrate evaporated to an oil under vacuum; yield: 0.65 g (99%) which was used without further purification; $v_{max}$/cm$^{-1}$ (film): 2931, 2857 (CH$_2$, asym., sym.), 2275 (NCO); $^1$H-NMR, d$_H$: 1.03 (9H, s, t-Bu), 4.76 (2H, s, CH$_2$), 7.23 (2H, d, J=8.38, H$_{arom3+5}$), 7.35 (2H, d, H$_{arom2+6}$), 7.37–7.48 (5H, m, Ph), 7.62–7.71 (5H, m, Ph); MS, (EI), (387.55); m/z: 330 (M - t-Bu, 52), 286 (M - t-Bu, M - t-Bu - NCO, 48), 199 (Ph$_2$SiOH$^+$, 100); C$_{24}$H$_{25}$NO$_2$Si.

N$^1$(4-tert-butyl-di-phenyl-silyl-O-benzyl)N$^3$(di-t-butyl-glutamyl) urea (18)

Method A: To a solution of di-tert-butyl-glutamate hydrochloride (0.46 g, 1.55 mmol) in THF (7 ml) was added triethylamine (0.31 g 3.10 mmol). The isocyanate, 15, (0.60 g, 1.55 mmol) in dry THF (3 ml) was added to the glutamate ester at room temperature. After 2 h the reaction mixture was filtered and evaporated to dryness under vacuum. The product was purified by column chromatography (EtOAc:cyclohexane 2:1) resulting in the oil, 16; yield 0.53 g (53%). $v_{max}$/cm$^{-1}$ (film): 3359 (NH), 2932, 2857 (CH$_2$, asym., sym.), 1729 (C=O, ester), 1670 (C=O, urea), 1154 (C—O, str.); $^1$H-NMR, d$_H$: 1.03 (9H, s, t-Bu), 1,40 (9H, s, t-Bu-glu), 1.43 (9H, s, t-Bu-glu), 1.68–2.00 (2H, 2m, CH(NH)CH$_2$), 2.18–2.32 (2H, 2m, CH$_2$CO$_2$-t-Bu), 4.08–4.12 (1H, m, CH(NH)CH$_2$), 4.68 (2H, s, CH$_2$), 6.38 (1H, d, J=8.12, NH—glu), 7.19 (2H, d, J=8.41, H$_{arom3+5}$), 7.32–7.47 (7H, m, Ph+H$_{arom2+6}$), 7.62–7.70 (5H, m, Ph), 8.54 (1H, s, NH—Ph); MS, (EI), (646.90); m/z: 540 (M - t-Bu+1, 2), 534 (M - 2t-Bu+2, 5), 478 (M - 3t-Bu+3, 100), 199 (Ph$_2$SiOH$^+$, 100); C$_{37}$H$_{50}$N$_2$O$_6$Si.

Method B: (one pot synthesis of compound 18) To a solution of di-tert-butyl-glutamate hydrochloride (4.14 g, 14.0 mmol) and triphosgene (1.39 g, 4.67 mmol) in toluene at −78° C., triethylamine (2.83 g, 28.0 mmol) in toluene (10 ml) was added dropwise over 30 min. The reaction was allowed to warm to room temperature. After 50 min, a solution containing (4-amino-benzyl)tert-butyl-diphenyl-silyl ether, 14 (5.00 g, 13.8 mmol) and triethylamine (1.95 ml, 14.0 mmol) was added over 5–10 min. After 20 h, the reaction mixture was filtered, washed sequentially with: H$_2$O (200 ml), aq HCl (1%, 200 ml), aq Na$_2$CO$_3$ (1%, 200 ml), H$_2$O (2×200 ml) dried (Mg$_2$SO$_4$) and evaporated to an oil under vacuum; yield: 9.90 g. This product was deprotected without further purification.

$N^1$(4-hydroxybenzyl)$N^3$(di-tert-butyl-glutamyl) urea (19)

From Method A: To a solution of 18, (0.53 g, 0.80 mmol) in THF (10 ml) was added tetra-butylammonium fluoride (2.5 ml, 2.5 mmol of 1M solution) in THF at room temperature. After 3 h, the reaction mixture was evaporated to dryness under vacuum. The product was dissolved in EtOAc (20 ml), washed with $H_2O$ (2×10 ml), dried ($MgSO_4$) and evaporated to an oil; yield: 0.40 g.

The deprotected compound, 19 (0.38 g), was purified by column chromatography (EtOAc:cyclohexane 3:1) resulting in an oil which crystallised on standing; yield 0.093 g (29%). $v_{max}/cm^{-1}$ (film): 3370 (broad, NH+OH), 2967 ($CH_3$), 2930, 2857 ($CH_2$, asym., sym.), 1716 (C=O, ester), 1678 (C=O, urea), 1153 (C—O, str.); $^1$H-NMR, $d_H$: 1.40 (9H, s, t-Bu), 1.42 (9H, s, t-Bu), 1.72–2.00 (2H, 2m, CH(NH)$CH_2$), 2.20–2.31 (2H, 2m, $CH_2CO_2$-t-Bu), 4.10–4.18 (1H, m, CH(NH)$CH_2$), 4.39 (2H, d, J=5.36, $CH_2$), 4.99 (1H, t, $CH_2$OH), 6.38 (1H, d, J=8.11, NH—glu), 7.16 (2H, d, J=8.35, $H_{arom3+5}$), 7.31 (2H, d, $H_{arom2+6}$), 8.50 (1H, s, NH—Ph); MS, (EI), (408.94); m/z: 408 ($M^+$, 10), 352 (M - t-Bu+1, 4), 296 (M - 2t-Bu+2, 14); $C_{21}H_{32}N_2O_6$.

From Method B: The one pot procedure yielded 18, which was purified by column chromatography; yield 2.57 g (46% over three steps) which was recrystallised from aq MeOH (60%).

$N^1$(4'-succinimidyl-oxy-carbonyl-oxy-benzyl)$N^3$(di-tert-butyl-glutamyl)urea (20).

To a solution of $N^1$(4'-hydroxy-benzyl)$N^3$(di-tert-butyl-glutamyl)urea, 19, (0.200 g, 0.49 mmol) and di-succinimidyl carbonate (0.128 g, 0.50 mmol) in 5.0 ml acetonitrile, 0.041 ml pyridine was added at once at room temperature. After 20 h the reaction mixture was evaporated to dryness under vacuum, the oily residue dissolved in 3.0 ml EtOAc, washed with $H_2O$ (3×3.0 ml), dried ($MgSO_4$) and evaporated again. 0.151 g of a semi-solid resulted, which was purified by column chromatography (eluent: EtOAc:cyclohexane 3:1). Finally 0.088 g (yield: 39%) of a solid resulted.

$V_{max}/cm^{-1}$ (film): 3369 (NH), 1783 (C=O, carbonate), 1726 (C=O, ester, ketone), 1660 (C=O, urea), 1207, 1156 (C—O, str.); $^1$H-NMR, $d_H$: 1.39 (9H, s, t-Bu), 1.42 (9H, s, t-Bu), 1.80–2.00 (2H, 2m, CH(NH)$CH_2$), 2.22–2.35 (2H, 2m, $CH_2CO_2$-t-Bu), 2.60 (4H, s, $CH_2$-succinimidyl), 4.10–4.20 (1H, m, CH(NH)$CH_2$), 4.89 (2H, s, $CH_2$), 6.47 (1H, d, J=8.10, NH—glu), 7.32 (2H, d, J=8.57, $H_{arom3+5}$), 7.40 (2H, d, $H_{arom2+6}$); MS, (549.58); m/z: 506($M^+$-$CO_2$+1,50), 450 ($M^+$-$CO_2$—$C_4H_8$+1, 18), 394 ($M^+$—$CO_2$-$2C_4H_8$+1, 60), 279 ($M^+$—$CO_2$-$2C_4H_8$,-hydroxysuccinimide +1,90); $C_{26}H_{35}N_3O_{10}$.

$N^1$[-{2(R)-[[2(4'-benzyloxy-carbonyl)-amino-3-mercantopropyl]-amino]-3-methyl-pentyl] isoleucylhomoserine Lactone] $N^3$(di-tert-butyl-glutamyl) urea (21)

To a solution of 9 in $CH_2Cl_2$ is added $N^1$(4-succinimidyl-oxycarbonyl-oxybenzyl)$N^3$(di-t-butyl-glutamyl) urea, 20 in dry THF and triethylamine at room temperature under $N_2$. The reaction mixture is evaporated, washed, dried ($MgSO_4$) and re-evaporated to 21.

$N^1$[(4-benzylidene-malononitrile-oxy-carbonyl)-4-oxy benzyl]$N^3$glutamyl urea (22)

Compound, 21 is dissolved in formic acid (95%), at 4° C. under $N_2$. After 22 h the solvent is evaporated under vacuum (pump) to give 22.

What is claimed is:

1. A compound of formula (XVI):

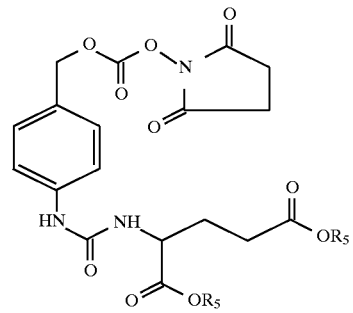

(XVI)

wherein $R_5$ is $C_{1-6}$ alkyl.

2. A compound according to claim 1 wherein $R_5$ is ethyl or t-butyl.

3. A compound of the formula:

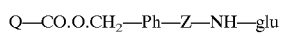

where Q is —O—(N-succinimide);

Ph is a phenylene ring which may be substituted by from 1 to 4 groups which may be the same or different and are selected from fluorine, chlorine, bromine, iodine, hydroxy, mercapto, amino, nitro, $C_{1-4}$alkyl, $C_{1-4}$haloalkyl, $C_{1-4}$alkoxy, $C_{1-4}$haloalkoxy, $C_{2-4}$alkenyl, $C_{2-4}$alkynyl and $C_{2-4}$haloalkenyl;

Z is —O.CO— or —NH—CO—; and glu is the residue of glutamic acid or a di-$C_{1-6}$alkyl ester thereof.

4. A compound of the formula:

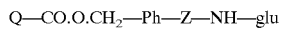

where Q is —O—(N-succinimide);

Ph is a phenylene ring which may be substituted by from 1 to 4 groups which may be the same or different and are selected from fluorine, chlorine, bromine, iodine, hydroxy, mercapto, amino, nitro, $C_{1-4}$alkyl, $C_{1-4}$haloalkyl, $C_{1-4}$alkoxy, $C_{1-4}$haloalkoxy, $C_{2-4}$alkenyl, $C_{2-4}$alkynyl and $C_{2-4}$haloalkenyl;

Z is —NH—CO; and glu is the residue of glutamic acid or a di-$C_{1-6}$alkyl ester thereof.

5. A method of preparing a prodrug which comprises reacting an active pharmaceutical drug having at least one group —SH with a protecting group compound of the formula:

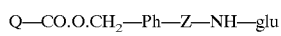

where Q is —O—(N-succinimide);

Ph is a phenylene ring which may be substituted by from 1 to 4 groups which may be the same or different and are selected from fluorine, chlorine, bromine, iodine, hydroxy, mercapto, amino, nitro, $C_{1-4}$alkyl, $C_{1-4}$haloalkyl, $C_{1-4}$alkoxy, $C_{1-4}$haloalkoxy, $C_{2-4}$alkenyl, $C_{2-4}$alkynyl and $C_{2-4}$haloalkenyl;

Z is —O.CO— or —NH—CO—; and glu is the residue of glutamic acid or a di-$C_{1-6}$alkyl ester thereof;

under conditions wherein the residue —CO.O.$CH_2$— PH—Z—NH—glu of said protecting group becomes linked to the drug by attachment to the sulfur atom of said —SH group, in place of the hydrogen thereof.

6. A method of preparing a prodrug which comprises reacting an active pharmaceutical drug having at least one group —SH with a protecting group compound of the formula:

Q—CO.O.CH$_2$—Ph—Z—NH—glu where Q is —O—(N-succinimide);

Ph is a phenylene ring which may be substituted by from 1 to 4 groups which may be the same or different and are selected from fluorine, chlorine, bromine, iodine, hydroxy, mercapto, amino, nitro, C$_{1-4}$alkyl, C$_{1-4}$haloalkyl, C$_{1-4}$alkoxy, C$_{1-4}$haloalkoxy, C$_{2-4}$alkenyl, C$_{2-4}$alkynyl and C$_{2-4}$haloalkenyl;

Z is —NH—CO—; and glu is the residue of glutamic acid or a di-C$_{1-6}$alkyl ester thereof;

under conditions wherein the residue —CO.O.CH$_2$—PH—Z—NH—glu of said protecting group becomes linked to the drug by attachment to the sulfur atom of said —SH group, in place of the hydrogen thereof.

* * * * *